(12) United States Patent
Bushby (10) Patent No.: US 8,414,511 B2
(45) Date of Patent: Apr. 9, 2013

(54) SYSTEM FOR TREATMENT OF PLANTAR FASCIITIS

(76) Inventor: Donald P. Bushby, Houston, TX (US)

( * ) Notice: Subject to any disclaimer, the term of this patent is extended or adjusted under 35 U.S.C. 154(b) by 1836 days.

(21) Appl. No.: 10/817,172

(22) Filed: Apr. 2, 2004

(65) Prior Publication Data

US 2005/0228332 A1 Oct. 13, 2005

(51) Int. Cl.
*A61F 5/00* (2006.01)
*A61F 13/06* (2006.01)
*B29D 11/00* (2006.01)
*A43B 13/34* (2006.01)

(52) U.S. Cl. ............. 602/1; 523/108; 36/35 R; 602/61

(58) Field of Classification Search .............. 602/23, 602/28, 29; 36/145, 150, 154, 160, 161, 36/174
See application file for complete search history.

(56) References Cited

U.S. PATENT DOCUMENTS

| | | | |
|---|---|---|---|
| 1,980,621 A * | 11/1934 | Innis | 36/11.5 |
| 2,985,970 A | 5/1961 | McCarthy | |
| 3,449,844 A * | 6/1969 | Spence | 36/44 |
| 4,997,709 A * | 3/1991 | Huddleston et al. | 428/344 |
| 5,865,779 A | 2/1999 | Gleason | |
| 5,897,518 A * | 4/1999 | Shaw | 602/65 |
| 6,120,473 A | 9/2000 | Oliverio | |
| 6,640,465 B1 * | 11/2003 | Burgess | 36/15 |
| 6,641,550 B1 | 11/2003 | Johnson | |
| 6,684,442 B1 | 2/2004 | Parker | |
| 2002/0188239 A1 * | 12/2002 | Turtzo | 602/27 |
| 2003/0145495 A1 * | 8/2003 | Green | 36/145 |
| 2004/0118017 A1 * | 6/2004 | Dalton et al. | 36/44 |
| 2004/0261294 A1 * | 12/2004 | Kawata | 36/44 |
| 2005/0011084 A1 * | 1/2005 | Stephenson | 36/15 |

FOREIGN PATENT DOCUMENTS

| | | |
|---|---|---|
| EP | 0 621 023 A2 | 10/1994 |
| WO | WO 80/01758 | 9/1980 |
| WO | WO 02/43517 A1 | 6/2002 |
| WO | WO 02/43518 A2 | 6/2002 |
| WO | WO 02/43519 A1 | 6/2002 |

OTHER PUBLICATIONS

PCT International Search Report and Written Opinion. Sep. 22, 2005.
Website http://www.dreamyfeet.co.uk/adhesive_padding.htm.
http://www.sportsinjuryclinic.net/cybertherapist/front/foot/plantarfasciitis/plantartaping.php Mar. 10, 2004.

* cited by examiner

*Primary Examiner* — Patricia Bianco
*Assistant Examiner* — Tarla Patel
(74) *Attorney, Agent, or Firm* — Kenneth A. Roddy (57) ABSTRACT

An stretch resistant plantar fascia support system is provided. The stretch resistant plantar fascia support system is adhesively applied to the foot of a patient for providing relief from plantar fasciitis. A portion of the stretch resistant plantar fascia support system is adhesively attached to the bottom surface of the foot for reducing stress on the plantar fascia.

36 Claims, 5 Drawing Sheets

SYSTEM FOR TREATMENT OF PLANTAR FASCIITIS

BACKGROUND OF THE INVENTION

The present invention generally relates to a stretch resistant plantar fascia support system. More particularly, the present invention relates to a stretch resistant plantar fascia support system that may be adhesively applied to a foot to provide relief from plantar fasciitis.

Figure 1:
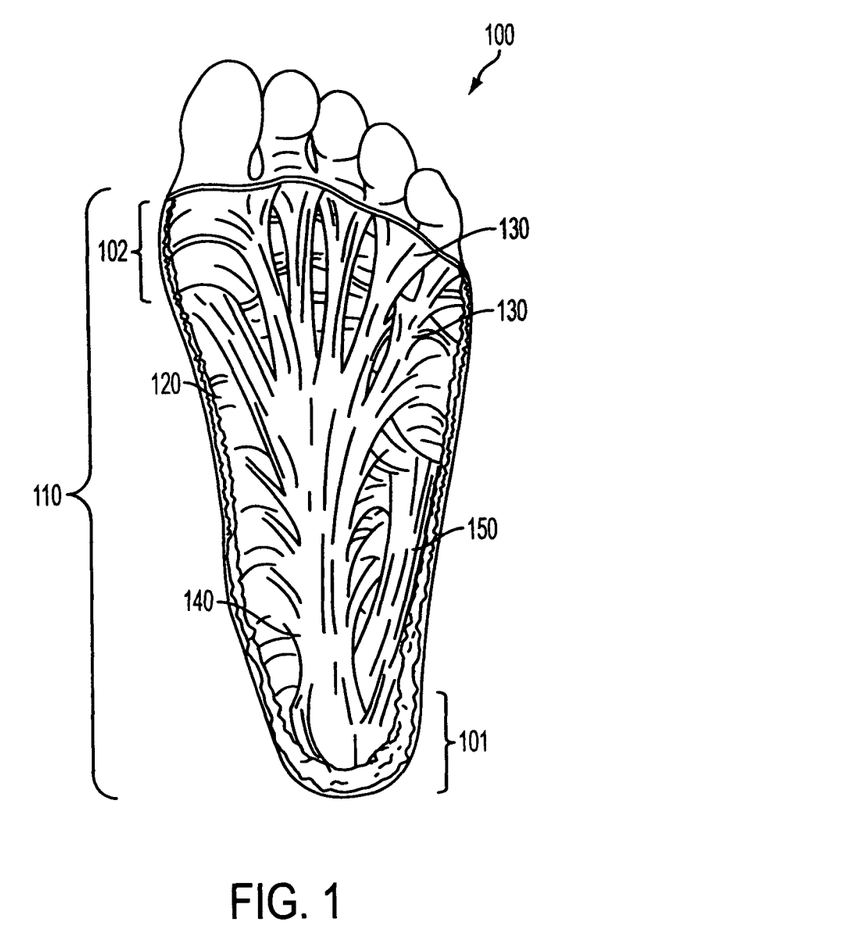
FIG. 1 illustrates parts of a plantar fascia in a dissected bottom view of a human foot.

FIG. 1 is a dissected bottom view of a human foot 100 provided to illustrate some of the parts of a plantar fascia 110 located in the bottom of the human foot 100. As shown in FIG. 1, the plantar fascia 110 extends from about the location of the heel 101 to about the location of the ball 102 of the foot. The plantar fascia 110 includes medial plantar fascia 120, superficial tracts 130, a central component of the plantar fascia 140, and a lateral component of the plantar fascia 150. The separate portions of the plantar fascia 110 act as a shock absorber while walking and transfer tensile forces along the bottom of the foot 100.

Figure 2:
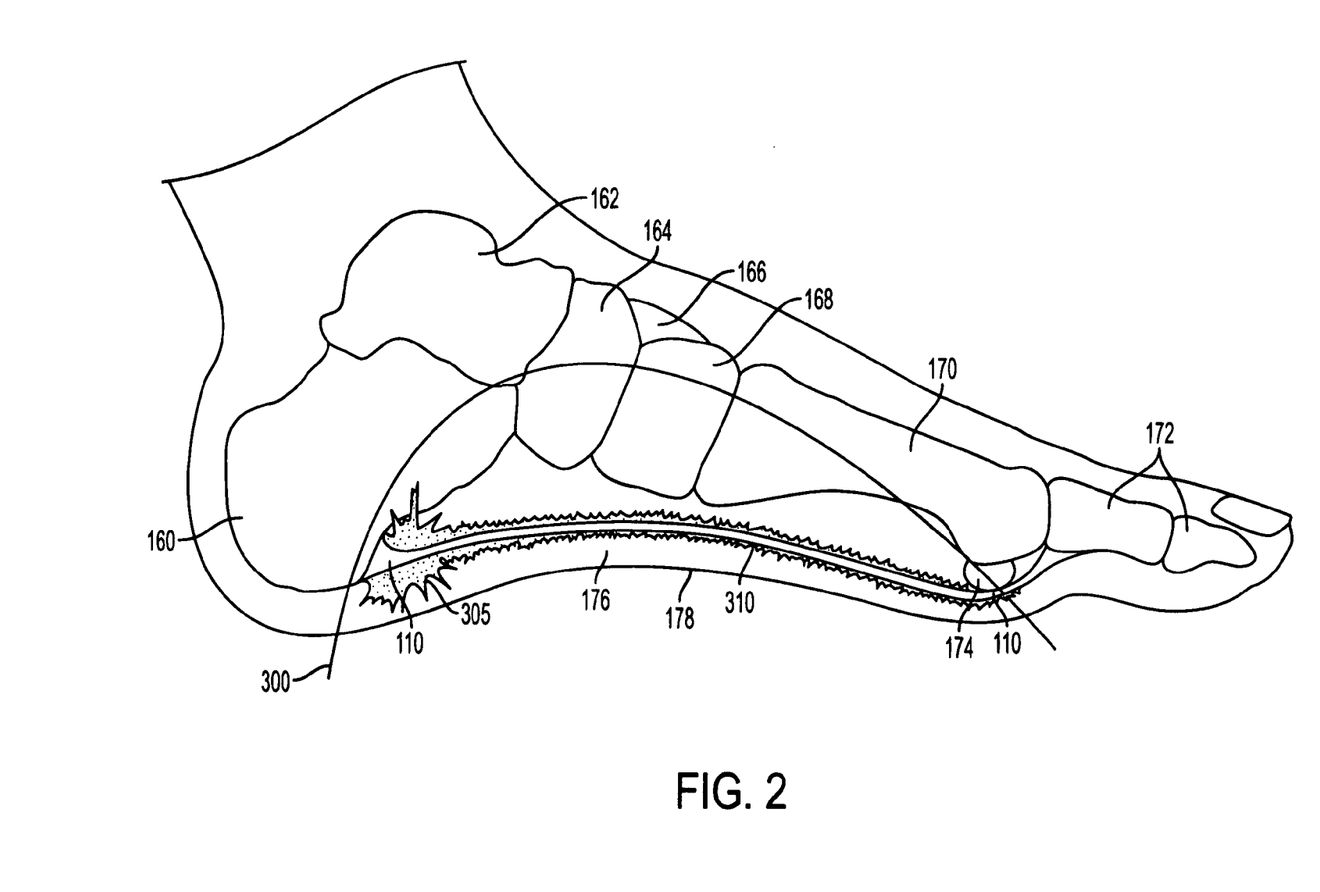
FIG. 2 illustrates a simplified side view of tissue and bone structure in the human foot.

FIG. 2 illustrates a simplified side view of tissue and bone structure in the human foot 100. As shown in FIG. 2, the human foot 100 includes the plantar fascia 110, a plantar calcaneus 160, a talus 162, a navicular 164, a cuneiform 166, a cuboid 168, metatarsals 170, phalanges 172, a sesamoid 174, a fat pad area 176, and an outer skin surface 178. From the side view in FIG. 2, the plantar calcaneus 160, the talus 162, the navicular 164, the cuneiform 166, the cuboid 168, the metatarsals 170, and the sesamoid 174 form what resembles the shape of an arch. This shape is commonly referred to as the longitudinal arch. Another arch commonly referred to as the transverse arch (metatarsal) also exists in about the same area in a perpendicular direction that runs laterally across the width of the foot.

The plantar fascia 110 serves the vital role of maintaining the shape of the two anatomical arches of the foot, the transverse arch and the longitudinal arch. As illustrated in FIGS. 1 and 2, the plantar fascia 110 runs across the bottom of the foot 100 from the heel 101 to the ball 102 and spreads out across the width of the foot 100. As longitudinal and lateral tensile stresses are produced in the bottom of the foot 100, the plantar fascia 110 absorbs the tensile forces and maintains the shape of the two anatomical arches.

For example, while standing or while in motion, forces experienced by the foot 100 act in a direction which tends to flatten the arches. The stress line 300 in FIG. 2 shows an approximation of the line of forces transferred through foot 100 during typical motion. As shown in FIG. 2, the stress line 300 resembles the shape of an archer's bow. The plantar fascia 110 running along near the bottom surface of the foot 100 is analogous to a string in the archer's bow. Forces that tend to move the ends of the bow apart increase tension on the string. In other words, as forces on the arch push the bones downward, the plantar fascia 110 is subjected to tensile forces.

If the tension on the plantar fascia 110 becomes excessive, the plantar fascia 110 may be damaged and produce a condition called plantar fasciitis. Plantar fasciitis is a painful medical condition resulting from inflammation of the plantar fascia 110. The plantar fascia 110 is thick and essentially inelastic. Overstressing the plantar fascia 110 may produce tears in the plantar fascia 110 or separate the plantar fascia 110 from bone and other surrounding materials. Tearing and separation of the plantar fascia 110 produces the painful inflammation known as plantar fasciitis. Frequently, the inflamed areas 305 are along the arch of the foot 100 or near the heel 101 of the foot 100 as shown in FIG. 2.

Plantar fasciitis may be quite debilitating in that everyday activities such as walking and standing may be very painful. Typical treatments for plantar fasciitis may involve oral anti-inflammatories, ice packs, bedrest, stretching, steroid injections, night splints and wedge-shaped arch supports. In extreme cases, treatment of plantar fasciitis may require corrective surgery.

For example, a design for an orthotic device for treatment of plantar fasciitis is disclosed in Gleason, U.S. Pat. No. 5,865,779. The device of Gleason is an elastic sock that is worn on a patient's foot. The elastic sock exerts compressive forces along the longitudinal and transverse axes of the patient's foot.

While some patients may be willing to wear an elastic sock, the elastic sock is both inconvenient and cumbersome. In order to be installed on the foot, the elastic sock must be stretched to fit over the heel and toe of the foot. Because the sock is elastic, the sock allows the foot to move and stretch. Consequently, the plantar fascia may still be subjected to excessive tensile forces during the critical heeling process. Re-subjecting the plantar fascia to tensile forces before it has completely healed may re-aggravate damaged portions of the plantar fascia and undermine the healing process.

In addition, the elastic sock is meant to be worn multiple times and may require regular cleaning to avoid odors and foot infections. Also, the sock may not fit inside a shoe while being worn and may be considered unsightly while walking around with bare feet. Consequently, the elastic sock does not prevent excessive stretching of the plantar fascia and is both inconvenient and cumbersome.

Another typical example of treatment for plantar fasciitis includes medical personnel strapping strips of tape to the bottom of an injured foot. Strips of tape are applied at various angles across the bottom of the foot. The tape is difficult to remove from the rolls and bunches up during the taping process. Thus, care must be exercised during the application of the tape to avoid blister-causing wrinkles in the tape and other problems.

As the patient walks with the taped foot, the tape works loose and stretches with time. In addition, the tape cannot be effectively applied by the patient to the patient's own foot and requires application by another individual such as a trained medical technician. Consequently, taping the foot is cumbersome, inefficient, and ineffective in preventing excessive stretching of the plantar fascia.

Sometimes when current methods of treatment for plantar fasciitis are ineffective, expensive surgical procedures are required to relieve the pain of plantar fasciitis. To get at the plantar fascia, surgeons may perform either an endoscopic procedure requiring small incisions or conventional direct visualization requiring the underside of the foot to be opened up. With either painful procedure, scars may result and recovery time may be from weeks to months.

Even with treatment, improper treatment of plantar fasciitis may lead to other medical problems. For example, if inflammation near the heel is allowed to continue for a long period of time, calcium deposits may build-up in the damaged region. As the calcium builds-up, bony outcroppings may develop in the heel that are commonly referred to as "heel spurs". The longer the plantar fascia remains inflamed around the heel, the stronger the conditions are for the development of heel spurs. Protrusion of the heel spurs into the surrounding tissue may result in a cycle of irritation, inflammation, and pain known as heel spur syndrome.

Heel spur syndrome is commonly treated with a surgical procedure requiring removal of the heel spurs from within the foot. An endoscopic procedure is typically not used for removal of heel spurs and open surgery is typically required. Recovery time from such surgery may range from weeks to months, during which time the patient has to curtail the amount of stress placed on the foot.

Thus, it may be highly desirable to have a system for avoiding and/or treating the pain of plantar fasciitis. It may also be highly desirable to have a system for treating plantar fasciitis that is economical and may be easily applied by the patient. It may also be highly desirable to have a system for treating plantar fasciitis that is discretely attached to the sole of the patient's foot and includes a substantially stretch resistant material to reduce tensile forces in the plantar fascia.

BRIEF SUMMARY OF THE INVENTION

A preferred embodiment of the present invention provides a system for treatment of plantar fasciitis. The system is economical and may be easily applied by a patient.

A stretch resistant plantar fascia support system is provided with a foot sole support. The foot sole support may be a thin one-piece device made of a uniform substantially stretch resistant material of a uniform thickness or the foot sole support may be made with a strip of substantially stretch resistant material bounded by a more deformable material. The foot sole support may be shaped to conform to the outline of the bottom of a foot or shaped to cover only a portion of the bottom of a foot. Straps and tabs may be included with the foot sole support for providing additional support to both the foot and other portions of the stretch resistant plantar fascia support system. The foot sole support, straps, and tabs have adhesive applied to portions of the surface of the foot sole support, the straps, and the tabs. Removable protective covers are applied over the adhesive and the removable protective covers may include indicia signifying the order in which the portions of the stretch resistant plantar fascia support system are to be applied to the foot.

To relieve the symptoms of plantar fasciitis, tensile stresses in the plantar fascia are reduced. The tensile stresses in the plantar fascia are reduced by adhering the foot sole support to the foot of the patient. The foot sole support absorbs tensile stress in the lower foot thereby reducing the tensile stress experienced by the plantar fascia and surrounding tissues. The straps and tabs may be attached in the prescribed order to the foot sole support and wrapped around or attached to portions of the foot to provide additional support to the stretch resistant plantar fascia support system.

DETAILED DESCRIPTION OF THE INVENTION

Figure 3:
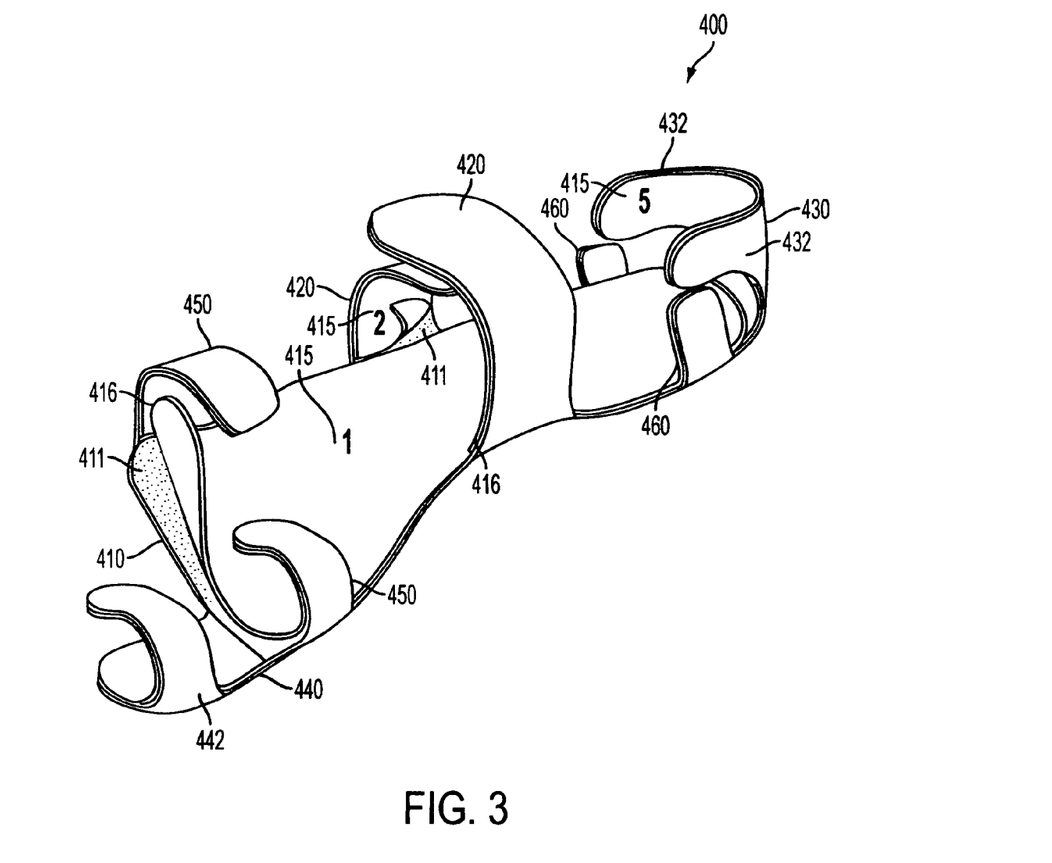
FIG. 3 illustrates a stretch resistant plantar fascia support system in accordance with an embodiment of the present invention.

FIG. 3 illustrates a stretch resistant plantar fascia support system 400 in accordance with an embodiment of the present invention. The stretch resistant plantar fascia support system 400 includes a foot sole support 410, an adhesive layer 411, indicia 415, removable protective covers 416, arch straps 420, heel strap 430, heel strap tabs 432, toe strap 440, toe strap tab 442, front straps 450, and heel tabs 460.

The arch straps 420, the heel strap 430, the toe strap 440, the front straps 450, and the heel tabs 460 are connected to the foot sole support 410. The arch straps 420 project from the sides of the foot sole support 410 approximately midway along the longitudinal axis of the foot sole support 410. The heel strap 430 projects from the back edge of the foot sole support 410 and the heel strap tabs 432 project from the sides of the heel strap 430. The toe strap 440 projects from the front edge of the foot sole support 410 and the toe strap tab projects from a side of the toe strap 440. The front straps 450 project from the sides of the of the foot sole support 410 adjacent the front edge of the foot sole support 410. The heel tabs 460 project from the sides of the foot sole support 410 adjacent the back edge of the foot sole support 410.

The adhesive layer 411 is applied to the top or inner surface of the foot sole support 410, the arch straps 420, the heel strap 430, the toe strap 440, the front straps 450, and the heel tabs 460. The removable protective covers 416 are removably adhered to the adhesive layer 411. Indicia 415 are printed on the removable protective covers 416.

In operation, the stretch resistant plantar fascia support system 400 is adhesively attached to a human foot 100. To adhesively attach the stretch resistant plantar fascia support system 400 to the human foot 100, the removable protective cover 416 adhered to the top of the foot sole support 410 is removed. The foot sole support 410 is pressed against the outer skin surface 178 on the bottom of the human foot 100.

Adhesion of the foot sole support 410 to the outer skin surface 178 on the bottom of the human foot 100 prevents extension and stretching of tissue on the bottom of the foot. By restricting extension of the tissue on the bottom of the foot, the level of tensile stress on the plantar fascia is reduced.

In the alternative, adhesive may be applied to select portions of the foot sole support 410, the straps 420, 430, 440 and 450, and the tabs 432, 442, and 462. For example, to reduce the chance of irritation to sensitive skin regions along an arch of the foot or to accommodate users with high arches, adhesive may only be applied to the portion of the foot sole support 410 contacting the ball of the foot and the heel of the foot.

In another alternative embodiment, adhesive may be applied to the sole of the foot. For example, adhesive sprays may be used to spray an adhesive layer on select portions of the foot. If a strong enough adhesive spray is used that would hold the foot sole portion 410 in place, then the stretch resistant plantar fascia support system 400 may be supplied without the adhesive layer 411 and removable protective covers 416.

To help maintain the position of the foot sole support 410 on the bottom of the human foot 100 and further reduce tensile stress on the plantar fascia, the arch straps 420 may be wrapped laterally over the arch of the foot. To install the arch straps 420, the removable protective cover 416 adhered to the inner surface of the arch straps 420 is removed. The arch straps 420 are then wrapped up and over the top of the foot 100. To secure the arch straps 420 in place, one of the arch straps 420 may overlap another arch strap 420 and be adhered to the outer surface of the other arch strap 420.

In the alternative, only one arch strap 420 may be used. With only one arch strap 420, the arch strap 420 may wrap laterally over the top of the arch and adhere to the bottom surface of the foot sole support 410 on the opposite side of the foot 100.

In another alternative embodiment, only one arch strap 420 may be used and the arch strap 420 may be separate and distinct from the foot sole support 410. With the foot sole support 410 already installed on the bottom of the foot 100, the arch strap 420 may be adhered to the foot sole support 410 on one side of the foot 100. The arch strap 420 may then be wrapped laterally over the arch, down the opposite side of the foot 100, and adhered to the foot sole support 410 on the opposite side of the foot 100.

Installation of the arch straps 420 also reduces stress on the plantar fascia. As presented earlier with regard to FIG. 2, the stress line 300 in FIG. 2 resembles an archer's bow. The stress line 300 passes through the talus 162, the navicular 164, the cuneiform 166, and the cuboid 168. Laterally wrapping the arch straps 420 over and around the top of the foot near the arch provides resistance to vertical and lateral movement of the talus 162, the navicular 164, the cuneiform 166, and the cuboid 168. Provision of the resistance to vertical and lateral movement by the arch straps 420 reduces flexure of the "bow" and related changes in stress on the plantar fascia.

To provide extra support to the heel of the human foot 100 and help maintain the position of the foot sole support 410 on the bottom of the human foot 100, the heel strap 430 may be adhered to the heel of the foot 100. To further support the heel and help maintain the position of the foot sole support 410, the heel strap 430 includes heel strap tabs 432. To install the heel strap 430 and heel strap tabs 432, the removable protective cover 416 adhered to the inner surface of the heel strap 430 and heel strap tabs 432 are removed. The heel strap 430 is then pressed against the back of the heel of the foot 100 and secured in place by contact between the adhesive layer 411 and the outer skin surface 178. The heel strap tabs 432 are pressed against the outer skin surface 178 along the sides of the heel of the foot 100.

In an alternative embodiment, the stretch resistant plantar fascia support system 400 may include a heel strap 430 without heel strap tabs 432. The heel strap 430 may be installed as described above by removing the removable protective cover 416 and adhering the heel strap 430 to the back of the heel.

Installation of the heel strap 430 provides extra support to the heel and helps maintain the position of the foot sole support 410. Adhesion of the heel strap 430 to the back of the heel provides an anchor point for the rear portion of the foot sole support 410. During the course of walking, the foot sole support 410 may be subjected to lateral and longitudinal forces from contact between the foot sole support 410 and other surfaces such as the interior of shoes or floor surfaces. Depending on the level of the lateral and longitudinal forces, the resistance to lateral and longitudinal forces provided by the adhesive layer 411 may be exceeded. Adhering the heel strap 430 to the heel of the foot 100 provides extra resistance to lateral and longitudinal forces that may otherwise cause the foot sole support 410 to shift around on the bottom of the foot.

Additionally, the heel strap 430 provides extra support to the heel of the foot 100. The human foot has a complex structure of tissue and bones. Tissues in the heel interact with other tissues in the foot to transfer forces exhibited during walking. As shown in FIG. 1, portions of the plantar fascia attach to the heel and other tissues that continue up around the back of the heel. Through these attachments, tissues in the heel transfer forces to and from the plantar fascia. Providing extra support to the heel of the foot 100 reduces the amount of stress transferred between the heel and the plantar fascia.

The stretch resistant plantar fascia support system 400 also includes heel tabs 460. Similar to the heel strap 430, the heel tabs 460 assist in maintaining the position of the foot sole support 410. To install the heel tabs 460, the removable protective covers 416 adhered to the inner surface of the heel tabs 460 are removed. The heel tabs 460 are then pressed against the sides of the heel of the foot 100 and secured in place by contact between the adhesive layer 411 and the outer skin surface 178. As the foot sole support 410 is subjected to lateral and longitudinal forces, the heel tabs 460 provide additional resistance to the lateral and longitudinal forces to help maintain the installed position of the foot sole support 410.

The stretch resistant plantar fascia support system 400 also includes front straps 450. The front straps 450 assist in maintaining the position of the foot sole support 410 and provide extra support to the area near the ball of the foot 100. To install the front straps 450, the removable protective covers 416 adhered to the inner surface of the front straps 450 are removed. The front straps 450 are then wrapped up and over the top of the foot 100. To secure the front straps 450 in place, one of the front straps 450 may overlap another front strap 450 and be adhered to the outer surface of the other front strap 450.

In the alternative, only one front strap 450 may be used. With only one front strap 450, the front strap 450 may wrap laterally over the top of the foot 100 and adhere to the bottom surface of the foot sole support 410 on the opposite side of the foot 100.

In another alternative embodiment, only one front strap 450 may be used and the front strap 450 may be separate and distinct from the foot sole support 410. With the foot sole support 410 already installed on the bottom of the foot 100, the front strap 450 may then be adhered to the foot sole support 410 on one side of the foot 100. The front strap 450 may then be wrapped laterally over the foot 100, down the opposite side of the foot 100, and adhered to the foot sole support 410 on the opposite side of the foot 100.

During the course of walking, the foot sole support 410 may be subjected to lateral and longitudinal forces from contact between the foot sole support 410 and other surfaces such as the interior of shoes or floor surfaces. Depending on the level of the lateral and longitudinal forces, the resistance to lateral and longitudinal forces provided by the adhesive layer 411 may be exceeded. Adhering the front straps 450 near the ball of the foot 100 provides extra resistance to lateral and longitudinal forces that may otherwise cause the foot sole support 410 to shift around on the bottom of the foot.

Installation of the front straps 450 also reduces stress on the plantar fascia. As shown in FIG. 1, portions of the plantar fascia attach to the ball of the foot and other portions such as the superficial tracts 130 continue past the ball of the foot 100 to the toe region. Due to the complex structure of tissue and bones in the human foot, tissues near the ball of the foot interact with other tissues in the foot to transfer forces induced during walking. Through the attachments near the ball of the foot, tissues near the ball of the foot transfer forces to and from the plantar fascia 110. Providing extra support near the ball of the foot 100 reduces the amount of stress transferred between the ball of the foot and the plantar fascia 110.

The stretch resistant plantar fascia support system 400 includes a toe strap 440. Installation of the toe strap 440 assists in maintaining the position of the foot sole support 410. To install the toe strap 440, the removable protective cover 416 adhered to the inner surface of the toe strap 440 is removed. The toe strap 440 is then pressed against the underside of the toe and the adhesive layer secures the toe strap 440 in place.

To further secure the toe strap 440 in place, the toe strap 440 includes a toe strap tab 442. To install the toe strap tab 442, the removable protective cover 416 adhered to the inner surface of the toe strap tab 442 is removed. The toe strap tab 442 is then wrapped up and over the top of the toe of the foot 100. The toe strap is wrapped back down the opposite side of the toe and adhered to the underside of toe strap 440 on the opposite side of the toe.

In the alternative, more than one toe strap tab 442 may be attached to the toe strap 440. For example, a second toe strap tab may be positioned opposite the toe strap tab shown in FIG. 3 on the opposite side of the toe strap 440. To install the toe strap tabs 442, the removable protective cover 416 adhered to the inner surface of the toe strap tabs 442 is removed. The toe strap tabs 442 are then wrapped up and over the top of the toe. To secure the toe strap tabs 442 in place, one of the toe strap tabs 442 may overlap the other toe strap tab 442 and be adhered to the outer surface of the other toe strap tab 442 similar to the arch straps 420 shown in FIG. 3.

In another alternative embodiment, only one toe strap tab 442 may be used and the toe strap tab 442 may be separate and distinct from the toe strap 440 and the foot sole support 410. With the toe strap 440 already installed on the bottom of the toe, the toe strap tab 442 may then be adhered to the toe strap 440 on one side of the toe. The toe strap tab 442 may then be wrapped laterally over the toe, down the opposite side of the toe, and adhered to the toe strap 440 on the opposite side of the toe.

The stretch resistant plantar fascia support system 410 may also include indicia 415 printed on the removable protective covers 416. The indicia 415 may represent instructions for the installation of the stretch resistant plantar fascia support system 410. For example, the indicia 415 may be numerical or alphabetic designations for the order in which portions of the stretch resistant plantar fascia support system 410 are to be installed. In FIG. 3, the indicia 415 on the removable protective cover 416 over the foot sole support 410 is the number "1" designating that the foot sole support 410 is to be installed first. The indicia 415 on the removable protective cover 416 on the arch straps 420 is the number "2" designating that the arch straps 420 are the next portion to be installed. Thus, the indicia may be increased or decreased incrementally to designate the order in which the portions of the stretch resistant plantar fascia support system 400 are to be installed.

In the alternative, letters or words may be used instead of numerals as the indicia 415 to designate the order in which the portions of the stretch resistant plantar fascia support system 400 are to be installed. For examples, letters "A", "B", and "C" or the words "First", "Second", and "Third" may be used to designate the order in which the first three portions are to be installed.

In the alternative, the indicia 415 may be printed on the various portions of the stretch resistant plantar fascia support system 400. For example, if an adhesive spray is applied to the skin rather than using an adhesive layer 411 and removable protective covers 416, the indicia 415 may be printed on the inner surface of components such as the foot sole support 410 and a consumer may still be able to see the indicia and determine the order of application.

In an alternative embodiment, the stretch resistant plantar fascia support system 400 may include the foot sole support 410 without the arch straps 420, the heel strap 430, the toe strap 440, and front strap 450 and the heel tabs 460. Similar to the embodiment shown in FIG. 3, the foot sole support 410 would be adhesively applied to the bottom surface of the foot.

In the alternative, the stretch resistant plantar fascia support system 400 may include various combinations of the arch straps 420, the heel strap 430, the toe strap 440, and front straps 450 and the heel tabs 460. For example, an alternative embodiment of the stretch resistant plantar fascia support system 400 may include the foot sole support 410 with arch straps 420. Another alternative embodiment of the stretch resistant plantar fascia support system 400 may include the foot sole support 410 with the heel strap 430. Yet another alternative embodiment of the stretch resistant plantar fascia support system 400 may include the foot sole support 410 with the toe strap 440. Consequently, various alternative embodiments of the stretch resistant plantar fascia support system 400 may be used that include the foot sole support 410 with different combinations of the arch straps 420, the heel strap 430, the toe strap 440, and front strap 450 and the heel tabs 460.

Figure 4:
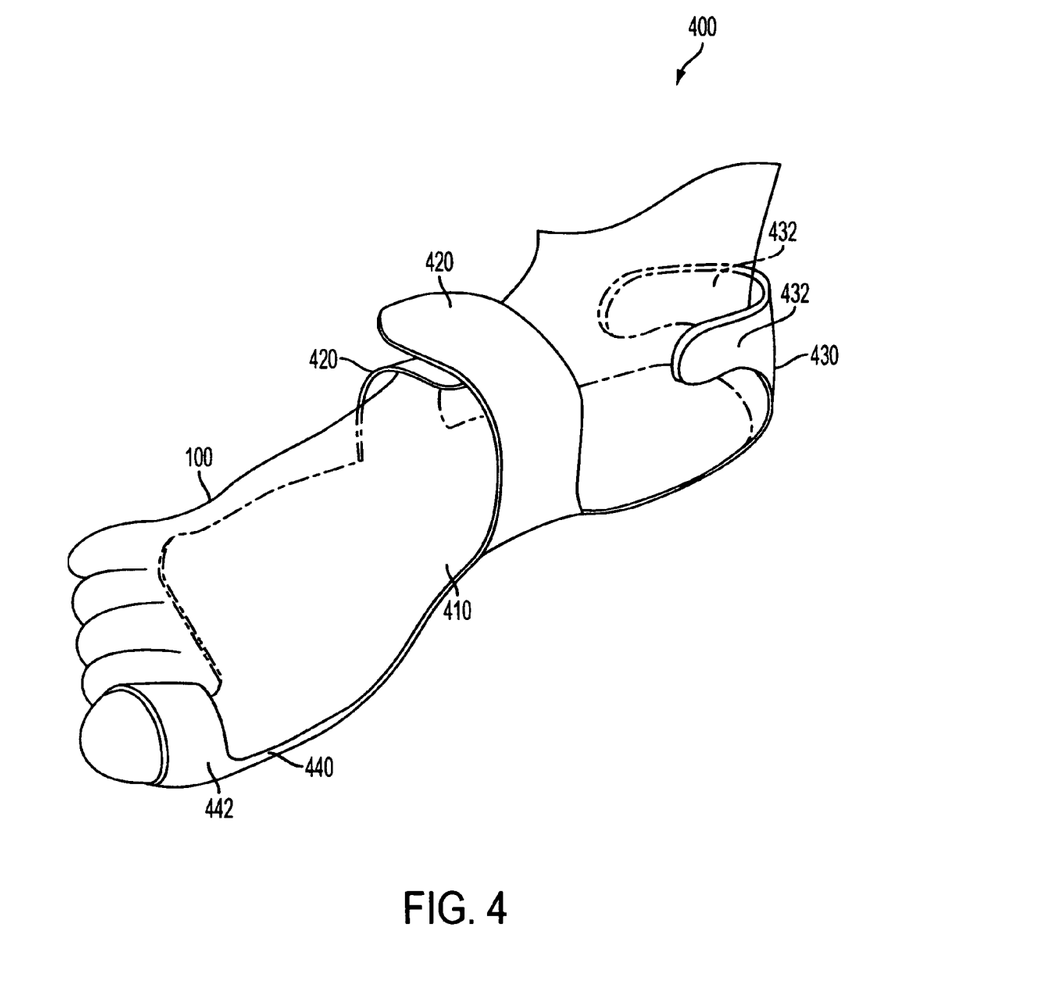
FIG. 4 illustrates a stretch resistant plantar fascia support system in accordance with an alternative embodiment of the present invention.

FIG. 4 illustrates a stretch resistant plantar fascia support system 500 as an alternative embodiment of the stretch resistant plantar fascia support system 400 of FIG. 3 installed on a human foot. The alternative embodiment shown in FIG. 4 includes a foot sole support 410, arch straps 420, heel strap 430, heel strap tabs 432, toe strap 440, and toe strap tab 442.

As shown in FIG. 4, the foot sole support 410 may be adhered to the sole of the foot to provide additional support to the region underneath the plantar fascia. The arch straps 420 may be wrapped around the top of the foot to provide additional support near the arch. The heel strap 430 may be adhered to the back of the heel to provide additional support to the heel and stabilize the position of the foot sole support 410. The toe strap 440 may be adhered to the bottom of the toe and the toe strap 442 wrapped around the toe to provide additional support to the toe and stabilize the position of the foot sole support 410.

Figure 5:
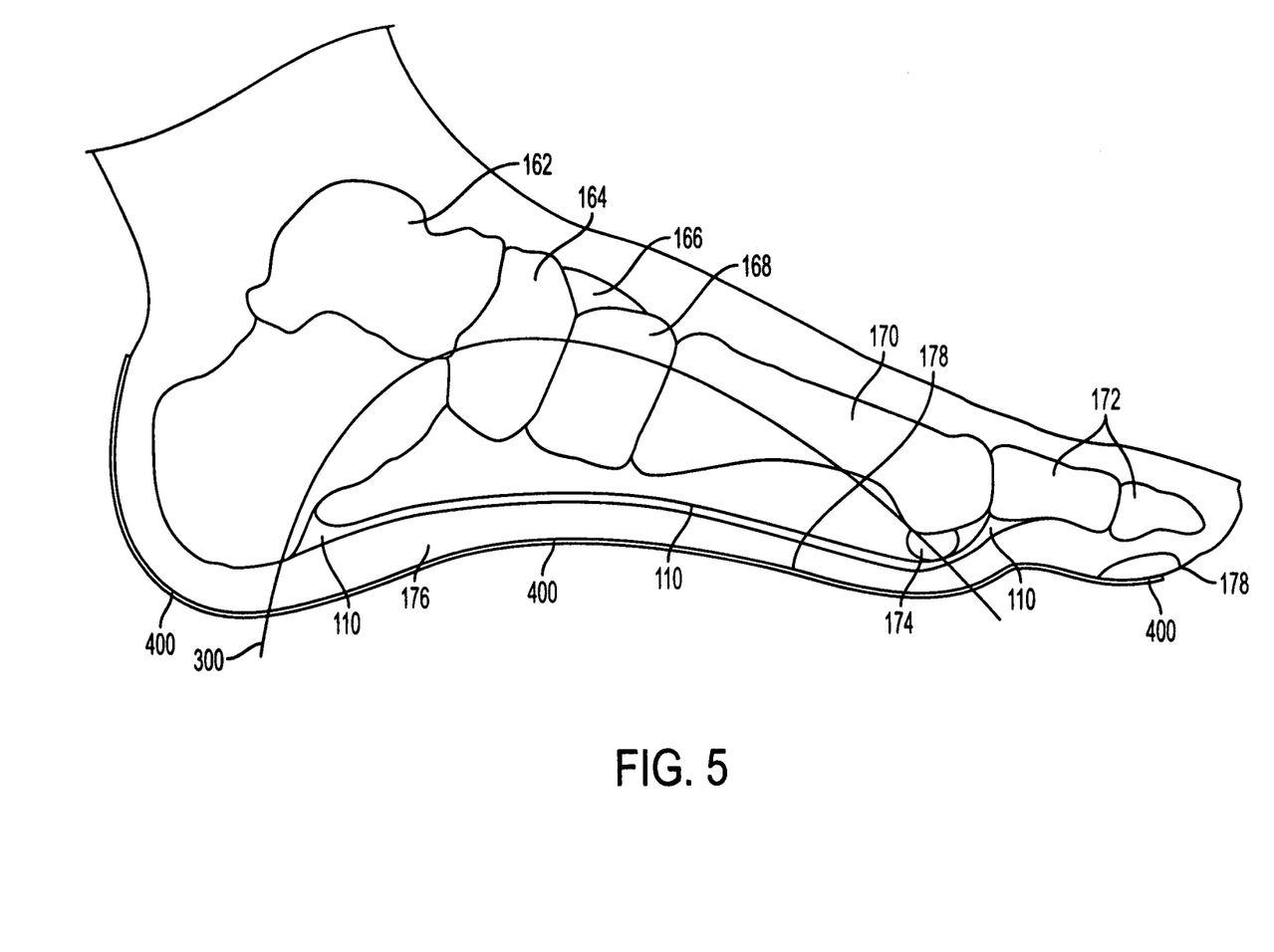
FIG. 5 illustrates stresses in the human foot with a stretch resistant plantar fascia support system installed in accordance with an embodiment of the present invention.

FIG. 5 illustrates stresses in the human foot 100 shown in FIG. 2 with a stretch resistant plantar fascia support system 400 attached to the human foot 100 in accordance with an embodiment of the present invention. As described previously with regard to FIG. 2, the stress line 300 shows an approximation of the line of forces transferred through a foot 100 during typical motion. The stress line 300 resembles the shape of an archer's bow. The plantar fascia 110 running along near the bottom surface of the foot 100 is analogous to a string in the archer's bow. Forces that tend to move the ends of the bow apart increase tension on the string. In other words, as forces on the arch push the bones downward, the plantar fascia 110 is subjected to tensile forces.

To reduce the tensile forces on the plantar fascia 110, the stretch resistant plantar fascia support system 400 is attached to the bottom of the foot. As depicted in FIG. 5, the stretch resistant plantar fascia support system 400 is analogous to another string in the archer's bow connected in parallel with the plantar fascia 110. Tensile forces induced in the bottom of the foot are shared between the plantar fascia 110 and the stretch resistant plantar fascia support system 400. Consequently, tensile force in the plantar fascia 110 is reduced and damaged areas may heal with a reduced likelihood of being subjected to excessive tensile forces.

Thus, a stretch resistant plantar fascia support system using a substantially stretch resistant material may be conveniently and easily applied to the foot of a patient by the patient for the treatment of plantar fasciitis. For example, the entire foot sole support, or portions of the foot sole support, of the stretch resistant plantar fascia support system may be made of a flexible material that exhibits less than 15 percent elongation when subjected to a 25 lb tensile load under test conditions specified in ASTM D3759. In addition, a material with a ratio of elongation to tensile strength (lb/in-width) that is less than 0.9 may be used to provide a balanced combination of strength and resistance to elongation.

Additionally, to simplify manufacturing and reduce cost, the stretch resistant plantar fascia support system may be made of a uniform material supplied in sheet form. Portions of the stretch resistant plantar fascia support system may be cut or punched from sheets of material. For example, the foot sole support may be shaped to resemble the outline of the sole of a left or right foot. Alternatively, the foot sole support may also be shaped for interchangeable use on either a left or right foot.

The stretch resistant plantar fascia support system may then be packaged individually, in multiples, or in a continuous package such as a roll with individual patches separated by perforations. For example, the individual packaging could be used by the average consumer for everyday use around the home. The continuous packaging could be used in high use situations such as locker rooms where access to stretch resistant plantar fascia support systems is required by multiple people.

The stretch resistant plantar fascia support system may be used while sleeping, while walking around with barefeet, or while wearing various types of footwear. Also, the stretch resistant plantar fascia support system non-invasively reduces the level of tensile stress carried by the plantar fascia and may prevent the need for complex and expensive surgery.

For example, a consumer may wake-up in the morning and experience pain along the bottom of the consumer's foot. The consumer may recognize the pain as plantar fasciitis and desire to treat the pain. Rather than schedule an appointment with a doctor and have to travel to the doctor's office for treatment, during which time the plantar fascia may be subjected to further excessive tensile stress, the consumer may desire to treat the pain at home.

With the stretch resistant plantar fascia support system of the present invention, the consumer may save the time, expense, and pain of traveling to a doctor's office for treatment. To use the stretch resistant plantar fascia support system, the consumer would simply remove the removable protective covers that protect the adhesive layer and apply the stretch resistant plantar fascia support system to the affected area.

While the above scenario described the consumer applying the stretch resistant plantar fascia support after waking up in the morning, the stretch resistant plantar fascia support system may also be worn to bed at night. By wearing the stretch resistant plantar fascia support system to bed at night, the stretch resistant plantar fascia support system may aid in the healing process while the consumer sleeps and protects the plantar fascia during the first few steps in the morning when stress is re-applied.

In addition, the stretch resistant plantar fascia support system may be comfortably worn when the consumer is not currently experiencing pain, but anticipates the potential for injury during a strenuous activity. For example, a consumer with a history of frequent occurrences of plantar fasciitis may desire to return to a strict exercise regiment following a prolonged period of inactivity. To avoid overstressing the plantar fascia until the foot has had enough time to become re-accustomed to the stresses of exercise, the consumer may desire to use the easily applied stretch resistant plantar fascia support system rather than some of the more cumbersome, less effective, and inconvenient alternatives such as taping and molded arch supports.

To aid the consumer with installation of the stretch resistant plantar fascia support system, the removable protective covers, or other portions of the stretch resistant plantar fascia support system, may include numerical indicia that indicate the order in which portions of the stretch resistant plantar fascia support system are applied to the foot. The consumer then applies the stretch resistant plantar fascia support system to the consumer's foot in the prescribed order.

In addition, the stretch resistant plantar fascia support system is comfortable and form fitting. The stretch resistant plantar fascia support system may be supplied for a plurality of foot sizes and the consumer may select the stretch resistant plantar fascia support system much like shoes are selected based upon standard shoe sizes. The foot sole support of the stretch resistant plantar fascia support system may even be shaped to conform to the shape of the sole of a foot. If an adjustment is needed to adapt the stretch resistant plantar fascia support system to an irregularity in a particular consumer's foot, the stretch resistant plantar fascia support system may be easily adapted by cutting the stretch resistant plantar fascia support system to accomodate the irregularity.

Because the stretch resistant plantar fascia support system is form fitting, the consumer may wear the stretch resistant plantar fascia support system in a variety of situations. For example, if a woven rayon microfiber with a 3600 thread count and/or thickness less than 30 mils is used, then the stretch resistant plantar fascia support system is thin enough to comply with contours of the foot and strong enough to provide adequate strength. While the consumer has the stretch resistant plantar fascia support system attached to the consumer's foot, the consumer has the option of walking around in bare feet, pulling a sock over the foot, or putting on shoes. The consumer may also wear the stretch resistant plantar fascia support system while using other additional devices such as arch supports, night splints, and custom orthotics.

Also, the stretch resistant plantar fascia support system does not interfere with rotation and movement of the ankle or calves. The stretch resistant plantar fascia support system is positioned beneath the ankle. The heel straps and the heel strap tabs are sized to avoid interference with the ankle bone. Because the stretch resistant plantar fascia support system is positioned beneath the ankle, contact between adhesive and leg hair is reduced. Thus, the need for shaving portions of the leg and ankle is reduced.

Also, different embodiments of the stretch resistant plantar fascia support system may be used depending on the type of footwear the consumer desires to wear while the stretch resistant plantar fascia support system is attached. For example, if the consumer is going to wear sandals, the consumer may desire to use a stretch resistant plantar fascia support system with a foot sole support and no adhesive straps or tabs to reduce the visibility of the stretch resistant plantar fascia support system. On the other hand, the consumer may desire to wear boots, where visibility of the stretch resistant plantar fascia support system is not an issue, and the consumer desires to have straps and tabs along with the foot sole portion for added stability.

The present invention may also include other items that can benefit a user. For example, to minimize the potential for skin damage and foot odor from the presence of moisture, the stretch resistant plantar fascia support system may be made of a permeable material. The stretch resistant plantar fascia support system may be made of a permeable material that wicks moisture away from the skin or the stretch resistant plantar fascia support system may include holes in the material to allow for the evaporation of moisture. In conjunction with the permeable material, adhesive may be applied in an intermittent manner to further increase the permeability and reduce the presence of moisture trapped between the foot and the stretch resistant plantar fascia support system. Also, the stretch resistant plantar fascia support system may include additives such as medicines, anti-fungal treatments, anti-microbial treatments, anti-inflammatory treatments, cooling compounds, heating compounds, deodorants, zeolite, perfumes, moisturizers, tee tree oil, talcum powder, and zinc oxide.

Thus, the present invention provides an effective system for the treatment of plantar fasciitis that is both economical and easy to use. The present invention provides a stretch resistant system that may be discretely attached to a patient's foot and reduces stress on the plantar fascia.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. An orthotic foot support device for a human foot, comprising:
   a foot support device having a thin flexible stretch-resistant sole member comprised of a single woven fabric layer of uniform thickness having a shape matching less than the entire outline of a sole of a wearer's foot to which the device is to be applied and sized to cover only a portion of the wearer's sole; and
   an adhesive layer on said sole member for securely adhering said device directly to an outer skin tissue on the sole of the foot, and at least one protective cover removably disposed over said adhesive layer which, when removed, exposes said adhesive layer;
   said stretch-resistant sole member sufficiently stretch-resistant to restrict extension and stretching of an outer skin tissue on the sole of a foot, when adhered thereto, and
   said adhesive layer of sufficient adhesion to maintain said stretch-resistant sole member in adhesive engagement with an outer skin tissue on the sole of the foot, such that tension forces applied to a plantar fascia are shared with an outer skin tissue, said adhesive layer, and said sole member to restrict extension and stretching of an outer skin tissue of a sole of a wearer's foot, whereby preventing excessive tensile stress in a plantar fascia.

2. The device according to claim 1, wherein
   said sole member has a ratio of elongation to tensile strength (lb/in-width) that is less than 0.9 to provide a balanced combination of strength and resistance to elongation.

3. The device according to claim 2, wherein
   said stretch-resistant sole member has a uniform thickness of less than 30 mils (0.762 mm).

4. The device according to claim 1, wherein
   said stretch-resistant sole member exhibits less than 15% elongation when subjected to a tensile load approximately equivalent to 25 pounds in accordance to ASTM D3759.

5. The device according to claim 1, further comprising:
   a thin flexible arch strap having opposed ends extending laterally outward from opposite sides of said stretch-resistant sole member;
   an adhesive layer on said arch strap for adhering said arch strap directly to an outer skin tissue on a side or top of an arch of a foot, and a protective cover removably disposed over said adhesive layer which, when removed, exposes said adhesive layer;
   said arch strap, when adhered to an outer skin tissue on a side or top of an arch of a foot, provides a further means to maintain said sole member in position on a sole of a foot of a wearer.

6. The device according to claim 5, wherein
   said arch strap is secured to said device by an adhesive.

7. The device according to claim 5, wherein
   said arch strap is integrally formed with said device.

8. The device according to claim 1, further comprising:
   at least one thin flexible heel strap extending rearwardly from said sole member of said device;
   an adhesive layer on said heel strap for adhering said heal strap directly to an outer skin tissue on a back of a heel of a foot, and a protective cover removably disposed over said adhesive layer which, when removed, exposes said adhesive layer;
   said heel strap, when adhered to an outer skin tissue of a heel of a foot provides a further means to maintain the position of said sole member on a sole of a foot.

9. The device according to claim 8, wherein
   said heel strap is integrally formed with said device.

10. The device according to claim 1, further comprising:
    a thin flexible front strap having opposed ends extending laterally outward from opposite sides of said stretch-resistant sole member in a position to at least partially overlap a top of a foot above a ball portion of a foot;
    an adhesive layer on said front strap for adhering said front strap directly to an outer skin tissue on a side and a top of a ball portion of a foot, and a protective cover removably disposed over said adhesive layer which, when removed, exposes said adhesive layer;
    said front strap, when adhered to an outer skin tissue on a side and a top of a ball portion of a foot provides a further means to maintain said sole member in position on the sole of a wearer's foot.

11. The device according to claim 10, wherein
    said front strap is integrally formed with said device.

12. An orthotic foot support device for a human foot, comprising:
    a foot support device having a thin flexible substantially stretch-resistant sole member comprised of a single woven fabric layer sized and shaped to engage an outer skin surface of at least a portion of a sole an individual's foot to which said device is to be applied and an adhesive layer on said sole member for adhering said sole member directly to an outer skin surface of a sole of a foot; and
    at least one thin flexible strap or tab having an end extending outward from said sole member beyond a sole of a foot, and an adhesive layer on said strap or tab for adhering said strap or tab directly to an outer skin surface on a side or a top of a foot, wherein said strap or tab adhered to an outer skin surface of a foot provides further means for maintaining said sole member in adhesive engagement with the skin tissue on a sole of a foot; said sole member is sufficiently stretch-resistant to restrict extension and stretching of an outer skin surface of a sole when adhered thereto and said adhesive layer on said sole member is of sufficient adhesion to maintain said sole member on an outer skin surface of a sole of a foot so that tension forces applied to a plantar fascia are shared with said outer skin surface, said adhesive layer, and said stretch resistant sole member to restrict stretching and extension of an outer skin tissue on a sole of a foot; whereby excessive or damaging tensile stress in a plantar fascia is prevented.

13. The device according to claim 12, wherein
said at least one thin flexible strap or tab comprises an arch strap having at least one end extending laterally outward from a side of said sole member in a position to engage a side and at least a portion of a top of an arch of a foot;
said arch strap, when adhered to an outer skin surface on the sides a side and a top of a arch of a foot, provides a further means to maintain said sole member in an adhesively engaged position with a sole of a foot.

14. The device according to claim 12, wherein
said at least one thin flexible strap or tab comprises at least one heel strap or heel tab extending from said sole engaging surface of said device, and an adhesive layer on said heel strap or heel tab for adhering said heel strap or heel tab directly to an outer skin surface on a heel of a foot;
said heel strap or heel tab, when adhered to an outer skin surface of a heel of a foot providing provides further means for maintaining said sole member in adhesive engagement with a sole of a foot.

15. The device according to claim 12, wherein
said at least one thin flexible strap or tab comprises a front strap having at least one end extending laterally outward from a side of said stretch-resistant sole member in a position to at least partially overlap a top of a foot above a ball portion of a foot, and an adhesive layer on said front strap for adhering said front strap directly to an outer skin surface surfaces on a side and a top of a ball portion of a foot;
said front strap, when adhered to an outer skin surface surfaces on a side and a top of a ball portion of a foot provides further means for maintaining said sole member in engagement with a sole of a foot.

16. The device according to claim 12, wherein
said stretch-resistant sole member has a thickness of less than 30 mils (0.762 mm) and exhibits less than 15% elongation when subjected to a tensile load approximately equivalent to 25 pounds in accordance with ASTM D3759.

17. A support device for a human foot, comprising:
a thin flexible foot support device of substantially uniform thickness having a stretch-resistant sole member comprised of a single woven fabric layer sized and shaped to engage and to cover an outer skin surface on at least a portion a sole of a wearer's foot and extend along at least a portion a plantar fascia region of the foot, an adhesive layer on said sole member for adhering said sole member directly to an outer skin tissue on a sole of a wearer's foot, and a protective cover removably disposed over said adhesive layer which, when removed, exposes said adhesive layer; and
a thin flexible arch strap member having a mid portion and opposed ends, an adhesive layer on said arch strap, and a protective cover removably disposed over said adhesive layer which, when removed, exposes said adhesive layer, wherein said arch strap when adhered to a foot provides a further means for maintaining said sole member in engagement with a sole of a wearer's foot; whereby
said adhesive layer on said sole engaging surface is of sufficient adhesion to maintain said device in place on the outer skin surface on the sole of the foot and said stretch-resistant sole engaging surface is sufficiently stretch-resistant to restrict extension and stretching of the outer skin surface on the sole of the foot, when adhered thereto, so that tension forces applied to a plantar fascia are shared with said outer skin surface, said adhesive layer and said sole engaging surface to restrict extension and stretching of a plantar fascia.

18. The support device according to claim 17, wherein
said stretch-resistant sole member exhibits less than 15% elongation when subjected to a tensile load equivalent to 25 pounds in accordance with test methods equivalent to ASTM D3759.

19. The device according to claim 18, wherein
said stretch-resistant sole member is comprised of a single layer of fabric with an adhesive layer wherein said fabric has a thickness of less than 30 mils (0.762 mm).

20. A method for restricting extension and stretching of the plantar fascia of a human foot, comprising the steps of:
providing a thin flexible device of substantially uniform thickness having a stretch-resistant sole member sized and shaped to be conformed to an outer skin tissue on at least a portion of a sole of a wearer's foot in a region of the foot from a heel of a foot to a distal end of the toes, excluding the region under the four smaller toes; and an adhesive layer on at least a portion of said sole member for adhering said device to the outer skin tissue on the sole of a wearer's foot, said adhesive layer of sufficient adhesive strength to maintain said device in place on the outer skin tissue on the sole of the foot and said stretch-resistant sole engaging surface sufficiently stretch-resistant so as to restrict extension and stretching of the outer skin tissue when adhered thereto;
adhering said sole member to an outer skin tissue on a portion of a sole of a foot such that tension forces applied to the plantar fascia are shared with said device outer skin tissue, said adhesive layer and said sole member to restrict extension and stretching of an outer skin tissue on a sole of a foot, whereby; preventing excessive stress on a plantar fascia.

21. The method according to claim 20, comprising the further steps of:
adhering opposed ends of a thin flexible arch strap extending laterally outward from opposite sides of said stretch-resistant sole member to the outer skin tissue on the sides or top of an arch of a foot to provide a further means for maintaining said stretch resistant sole member in adhesive contact with a sole of a foot.

22. The method according to claim 21, wherein
said steps of adhering said arch strap include a preliminary step of adhering a midportion of said arch strap to an underside of said device, and thereafter
adhering said opposed ends of said arch strap to an outer skin tissue on the sides or top of an arch of a foot in a position to at least partially encircle a talus, a navicular, a cuneiform, or a cuboid region of a foot.

23. The method according to claim 20, comprising the further steps of:
adhering a thin flexible heel strap extending from said sole member of said device to an outer skin tissue on a back or a side of a heel of a foot to provide a further means for maintaining said sole member in adhesive engagement with a sole of a foot.

24. The method according to claim 20, wherein
said sole engaging surface is sized and shaped to engage the outer skin tissue on a portion of the sole of a foot and to extend from a heel of a foot to about a ball portion of a foot, and comprising the further steps of:
adhering opposed ends of a thin flexible strap extending laterally outward from opposite sides of said stretch-resistant sole member to the outer skin tissue on a side or a top of a foot to provide a further means for maintaining said sole member in engagement with a sole of a foot; and wherein said device is used for the treatment or prevention of plantar fasciitis.

25. The method according to claim 20, comprising the further steps of:

removing at least one protective cover removeably disposed over said adhesive layer which, when removed, exposes said adhesive layer, and wherein said sole member is of a substantially uniform thickness of less than less than 30 mils (0.762 mm) and exhibits less than 15% elongation when subjected to a tensile load approximately equivalent to 25 pounds in accordance with the test methods of ASTM D3759.

26. An orthotic foot support device for reducing stress on the plantar fascia of a wearer's foot, said device comprising:

a stretch resistant, uniform thickness sole support, comprised of a single woven fabric layer having a shape matching less than an entire outline of a sole of an individual's foot where the device is to be applied;

an adhesive layer on said sole support for attaching said sole support to a sole of the wearer's foot such that said sole support absorbs tensile stress thus preventing extension and stretching of tissue on a bottom of the wearer's foot on which a said sole support is attached, whereby preventing excessive tensile stress in a plantar fascia.

27. The device of claim 26, wherein said device, further comprises;

a protective cover layer detachably disposed on said adhesive layer, a strap to be affixed to a foot generally transversely to said sole support;

an adhesive layer on said strap for adhering said strap to an outer skin surface of a top of the foot;

a protective cover layer detachably disposed on said strap.

28. The device of claim 26 wherein said sole support has a size less than the size of a entire sole of a wearers' foot, and wherein said sole support has a ratio of elongation to tensile strength (lb/in-width) that is less than 0.9 to provide a balanced combination of strength and resistance to elongation.

29. The device of claim 28 wherein said sole support single woven fabric layer is a woven micro-fiber layer.

30. The device of claim 28 wherein said sole support is less than 30 mils (0.762 mm) thick, whereby being thin enough to be worn inside socks or shoes.

31. An orthotic foot support device for reducing stress on the plantar fascia of a wearer's foot, said device comprising:

a thin flexible stretch resistant, sole support, shaped to cover only a portion the sole of a wearer's foot on which the device is to be applied; and wherein said sole support does not including a resilient cushion layer; and wherein said sole support has a ration of elongation to tensile strength (lb/in-width) that is less than 0.9 providing a balanced combination of strength and resistance to elongation;

an adhesive layer on said sole support for attaching said sole support to a sole of the wearer's foot so that extension and stretching of tissue on a bottom of the wearer's foot is restricted, whereby preventing excessive tensile stress in a plantar fascia.

32. The device of claim 31, wherein said device, further comprises;

a protective cover layer detachably disposed on said adhesive layer, a strap to be affixed to the wearer's foot with an end extending outwardly from said sole support;

an adhesive layer on said strap for adhering said strap to an outer skin surface of the wearer's foot;

a protective cover layer detachably disposed on said strap.

33. The device of claim 31 wherein said sole support includes a woven fabric layer which exhibits less than 15 percent elongation when subjected to a 25 lb tensile load under test conditions specified in ASTM D3759, wherein said device includes a protective cover removeably disposed on said adhesive layer and wherein said device is to be used in the treatment of plantar fasciitis or, in the prevention of excessive tensile stress in a plantar fasciitis.

34. A plantar fascia support device for a human foot comprising:

a uniform thickness, sole support, shaped to cover only a portion of a bottom of a wearer's foot where the device is to be applied, wherein said sole support has a ratio of elongation to tensile strength (lb/in-width) that is less than 0.9 to provide a balanced combination of strength and resistance to elongation; and an adhesive layer on said sole support for securely adhering said sole support to an outer skin of a sole of the wearer's foot.

35. The device of claim 34 wherein said sole support is comprised of a single non-resilient support layer, a uniformly applied adhesive layer and a protective cover layer detachably disposed on said adhesive layer; and wherein said sole support exhibits less than 15 percent elongation when subjected to a 25 lb tensile load under test conditions equivalent to those specified in ASTM D3759.

36. The device of claim 34, wherein said device, further comprises;

a protective cover layer detachably disposed on said adhesive layer, a strap to be affixed to a wearer's foot generally transversely to said sole support;

an adhesive layer on said strap for adhering said strap to an outer skin surface of a top or a side of the wearer's foot;

a protective cover layer detachably disposed on said strap.

* * * * *